United States Patent

Yamasaki et al.

Patent Number: 5,847,074
Date of Patent: *Dec. 8, 1998

[54] PHOSPHOLIPASE C-INHIBITING PEPTIDES

[75] Inventors: Motoo Yamasaki; Genkichi Ishikawa, both of Machida; Yoshimi Honma, Tokyo, all of Japan

[73] Assignee: Kyowa Hakko Kogyo Co., Ltd., Tokyo, Japan

[*] Notice: The term of this patent shall not extend beyond the expiration date of Pat. No. 5,580,956.

[21] Appl. No.: 432,143

[22] PCT Filed: Sep. 8, 1994

[86] PCT No.: PCT/JP94/01486

§ 371 Date: May 5, 1995

§ 102(e) Date: May 5, 1995

[87] PCT Pub. No.: WO95/07293

PCT Pub. Date: Mar. 16, 1995

[30] Foreign Application Priority Data

Sep. 10, 1993 [JP] Japan .................................. 5-225397

[51] Int. Cl.$^6$ .................................................. C07K 9/00
[52] U.S. Cl. ........................................... 530/325; 530/327
[58] Field of Search ..................................... 530/327, 325

[56] References Cited

U.S. PATENT DOCUMENTS 5,580,956  12/1996  Saito et al. .............................. 530/325

FOREIGN PATENT DOCUMENTS

0584374A1  3/1994  European Pat. Off. .......... C07K 7/10

OTHER PUBLICATIONS

Rhee et al, Studies of Inositol Phospholipid–Specific Phospholipase C, *Science*, vol. 244, pp. 546–550, May 1989.

Homma et al, Isolation and Characterization of a γ–Type Phosphoinositide–Specific Phospholipase C(PLC–γ$_2$, ), *Biochem. J.*, vol. 269, pp. 13–18, 1990.

Anderson et al, Binding of SH2 Domains of Phospholipase Cγ1, GAP, and SRC to Activated Growth Factor Receptors, *Science*, vol. 250, pp. 979–982, Nov. 1990.

Brass et al, Regulation of the Phosphoinositide Hydrolysis Pathway in Thrombin–Stimulated Platelets by a Pertussis Toxin–Sensitive Guanine Nucleotide–Binding Protein, *The Journal of Biological Chemistry*, vol. 261, No. 36, pp. 16838–16847, Dec. 1986.

Cockcroft et al, Two G–Proteins Act in Series to Control Stimulus–Secretion Coupling in Mast Cells: Use of Neomycin to Distinguish Between G–Proteins Controlling Polyphosphoinositide Phosphodiesterase and Exocytosis, *The Journal of Cell Biology*, vol. 105, No. 6, Pt.1) pp. 2745–2750, Dec. 1987.

Smith et al, Receptor–Coupled Activation of Phosphoinositide–Specific Phospholipase C by an N Protein, *Science*, vol. 232, pp. 97–100, Apr. 1986.

Ross et al, Localization of PDGF–B Protein in Macrophages in All Phases of Atherogensis, *Science*, vol. 248, pp. 1009–1012, May 1990.

Kawahara et al, Platelet–Derived Growth Factor (PDGF)–Induced Phospholipase C–Mediated Hydrolysis of Phosphoinositides in Vascular Smooth Muscle Cells—Different Sensitivity of PDGF–and Angiotensin II–Induced Phospholipase C Reactions to Protein Kinase C–Activating Phorbol Esters, *Biochemical and Biophysical Research Communications*, vol. 156, No. 2, pp. 846–854, Oct. 31, 1988.

Homma, et al, Evidence for Involvement of Phospholipase C–γ2 in Signal Transduction of Platelet–Derived Growth Factor in Vascular Smooth–Muscle Cells, *Biochem. J.*, vol. 290, pp. 649–653, 1993.

Shimohama et al, Aberrant Accumulation of Phospholipase C–Delta in Alzheimer Brains, *American Journal of Pathology*, vol. 139, No. 4, pp. 737–742, Oct. 1991.

Homma et al, Inhibitory Effect of SRC Homology (SH) 2/SH3 Fragments of Phospholipase C–γ on the Catalytic Activity of Phospholipase C Isoforms, *The Journal of Biological Chemistry*, vol. 267, No. 30, pp. 21844–21849, Oct. 25, 1992.

Homma et al, Suppression of Membrane Phospholipase C Activity by Synthetic Autoinhibitor Peptides, *Methods: A Comparison to Methods in Enzymology* 5, 229–232 (1993).

Hanby, "Conformational Restrictions on Peptides" Life Sciences, v.31, pp. 189–199 (1982).

Konig, "Peptide Useful as Phospholipase Inhibitor" WPIDS Abstract #88–308965[44] (1988).

*Primary Examiner*—Cecilia J. Tsang
*Assistant Examiner*—Patrick R. Delaney
*Attorney, Agent, or Firm*—Morgan & Finnegan, L.L.P.

[57] ABSTRACT

The present invention relates to phopholipase C-inhibiting peptides which are represented by formula (I):

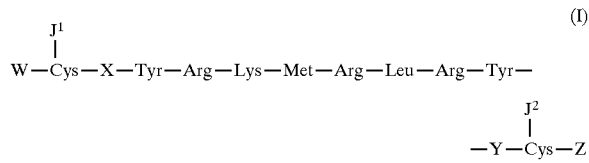

wherein $J^1$ and $J^2$ are each hydrogen or combined together to form a single bond; W is hydrogen, a substituted or unsubstituted alkanoyl, a substituted or unsubstituted aroyl or coumaryl; X is a single bond, -Leu- or -Ser-Leu-Val-Glu-Leu-Val-Ser-Tyr-Tyr-Glu-Lys-His-Ala-Leu- (at least one of the N-terminal 14 amino acid residues may be deleted); Y is a single bond or -Pro-Val-; and Z is hydroxy or amino.

9 Claims, No Drawings

PHOSPHOLIPASE C-INHIBITING PEPTIDES

TECHNICAL FIELD

The present invention relates to novel peptides which inhibit the phopholipase C (hereinafter referred to as "PLC") activity.

BACKGROUND ART

PLC, e.g., inositolphospholipid PLC (hereinafter referred to as "PI-PLC") was separated and purified from various tissues for the purpose of elucidation of intracellular signal transduction pathway and the existence of nine isozymes in four types ($\alpha$, $\beta$, $\gamma$ and $\delta$) has been demonstrated. Type $\gamma$ is known to occur in two kinds, $\gamma_1$ and $\gamma_2$ (S. G. Rhee et al., Science, 244, 546–550 (1989); Y. Homma et al., Biochem.J., 269, 13–18 (1990)). Both kinds have been shown to play an important role in signal transduction of growth factors. The structural feature of the $\beta$, $\gamma$ and $\delta$ types is that they contain an oncogene src-associated region, SH2/SH3 region, between I and II regions common to $\beta$, $\gamma$ and $\delta$. SH2 region in the $\gamma$ type is essential for the interaction with a receptor-type tyrosine kinase (D. Anderson et al., Science, 250, 979–982 (1990)). Although the function of SH3 region in the $\gamma$ type has not been clear, it is presumably important for the interaction with cytoskeletons. Recently, the oncogene crk having SH2/SH3 region but not kinase region was found and this has highlighted the possibility that the regulation disorder (abnormal activity of PI-PLC) and abnormal cell proliferation as mediated by SH2/SH3 region may induce tumor. There are many other reports that review the association of increased PLC levels with pathologic conditions:

PLC is associated with the system of platelet activation by thrombin (J. Biol. Chem., 261, 16838–16847 (1986)); PLC activity is associated with histamine release (J. Cell Biol., 105, 2745–2750 (1987)); PLC is associated with the system of signal transduction by a receptor for N-formyl-methionyl-leucyl-phenylalanine which is known to induce inflammation via granulocytes and polymorphonuclear leukocytes (PMN) (Science, 232, 97–100 (1986)); the $\beta$ chain of a platelet-derived growth factor (PDGF) is expressed in a large amount in arteriosclerotic lesions (Science, 248, 1009 (1990)); PLC-$\gamma_2$ is present as a component in the signal transduction system for the proliferation of PDGF-dependent vascular smooth muscle cells and hence is closely associated with the smooth muscle cell proliferation system (Biochem. Biophys. Res. Commun., 156, 846–854 (1988); Biochem.J., 290, 649–653 (1993)); and PLC is increased in Alzheimer's disease (Am. J. Pathol., 139, 737–742 (1991)). Hence, it is expected that the aforementioned diseases can be alleviated by inhibiting the PLC activity and there is a need for agents that inhibit the PLC activity.

The following peptides are disclosed in J. Biol. Chem., 267, 21844–21849 (1992) as being capable of inhibiting the PLC activity:

Ser-Leu-Val-Glu-Leu-Val-Ser-Tyr-Tyr-Glu-Lys-His-Ala-Leu-Tyr-Arg-Lys-Met-Arg-Leu-Arg-Tyr-Pro-Val,

Ser-Tyr-Tyr-Glu-Lys-His-Ala-Leu-Tyr-Arg-Lys-Met, Glu-Lys-His-Ala-Leu-Tyr-Arg-Lys-Met,

Glu-Lys-His-Ala-Leu-Tyr-Arg-Lys-Met-Arg-Leu-Arg-Tyr-Pro-Val,

Leu-Tyr-Arg-Lys-Met-Arg-Leu-Arg-Tyr-Pro-Val,

Tyr-Arg-Lys-Met-Arg-Leu-Arg-Tyr, and

Arg-Lys-Met-Arg-Leu-Arg.

DISCLOSURE OF THE INVENTION

According to the present invention, phopholipase C-inhibiting peptides which are represented by formula (I) (hereinafter referred to as "Compound(s) (I)") can be provided:

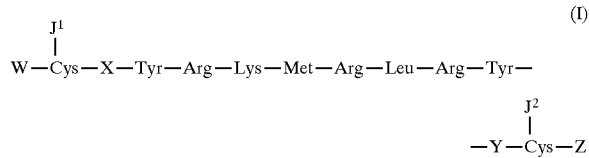

wherein $J^1$ and $J^2$ are each hydrogen or combined together to form a single bond; W is hydrogen, a substituted or unsubstituted alkanoyl, a substituted or unsubstituted aroyl or coumaryl; X is a single bond, -Leu- or -Ser-Leu-Val-Glu-Leu-Val-Ser-Tyr-Tyr-Glu-Lys-His-Ala-Leu- (at least one of the N-terminal 14 amino acid residues may be deleted); Y is a single bond or -Pro-Val-; and Z is hydroxy or amino.

In the definition of Compounds (I), the substituted or unsubstituted alkanoyl may be exemplified by those having 1–20 carbon atoms such as formyl, acetyl, propionyl, butyryl, isobutyryl, valeryl, isovaleryl, pivaloyl, caprylayl, lauroyl, myristoyl, palmitoyl, and stearoyl. Exemplary substituents include carboxy, alicyclic alkyl, and phenyl. Exemplary alicyclic alkyls include those having 3–8 carbon atoms such as cyclopropyl, cyclobutyl, cyclopentyl, and cyclohexyl. The substituted or unsubstituted aroyl may be exemplified by benzoyl and naphthoyl. Exemplary substitutents include hydroxy groups and the number of substituents is 1–3.

The abbreviations for the amino acids and their protective groups used herein follow the recommendations by IUPAC-IUB Commission on Biochemical Nomenclature (Biochemistry, 11, 1726 (1972)).

The abbreviations for the amino acids and protective groups are as follows.

Val:L-Valine
Leu:L-Leucine
Lys:L-Lysine
Met:L-Methionine
Arg:L-Arginine
Tyr:L-Tyrosine
Cys:L-Cysteine
Pro:L-Proline
t-Boc:t-Butyloxycarbonyl
t-Bu:t-Butyl
Fmoc:9-Fluorenylmethyloxycarbonyl
Pmc:2,2,5,7,8-Pentamethylchroman-6-sulfonyl
Trt:Trityl The abbreviations for the side-chain protected amino acids are as follows.

Fmoc-Tyr(t-Bu)-OH: $N^\alpha$-9-Fluorenylmethyloxycarbonyl-O-t-butyl-L-tyrosine

Fmoc-Lys(t-Boc)-OH: $N^\alpha$-9-Fluorenylmethyloxycarbonyl-$N^{68}$-t-butyloxycarbonyl-L-lysine Fmoc-Arg(Pmc)-OH: $N^\alpha$-9-Fluorenylmethyloxycarbonyl-$N^\delta$-2,2,5,7,8-pentamethylchroman-6-sulfonyl-L-arginine Fmoc-Cys(Trt)-OH: $N^\alpha$-9-Fluorenylmethyloxycarbonyl-S-trityl-L-cysteine The abbreviations for the reaction solvents and reaction reagents are as follows.

PyBOP: Benzotriazol-1-yloxytripyrrolidinophosphonium hexafluorophosphate

HOBt: N-Hydroxybenzotriazole
NMM: N-Methylmorpholine
DMF: N,N-Dimethylformamide
TFA: Trifluoroacetic acid The manufacturer of the caboxylic acid used for N-terminus modification is as follows:

n.-Caprylic acid: TOKYO KASEI KOGYO CO., LTD.
Specific examples of compounds (I) are shown in Table 1.

TABLE 1

| COMPOUND NO. | SEQ ID NO: | SEQUENCE |
|---|---|---|
| (I-1) | 1 | H—Cys—Leu—Tyr—Arg—Lys—Met—Arg—Leu—Arg—Tyr—Pro—Val—Cys—NH$_2$ |
| (I-2) | 2 | H—Cys—Leu—Tyr—Arg—Lys—Met—Arg—Leu—Arg—Tyr—Pro—Val—Cys—NH$_2$ (cyclic S—S) |
| (I-3) | 3 | CH$_3$(CH$_2$)$_6$CO—Cys—Leu—Tyr—Arg—Lys—Met—Arg—Leu—Arg—Tyr—Pro—Val—Cys—NH$_2$ |
| (I-4) | 4 | CH$_3$(CH$_2$)$_6$CO—Cys—Leu—Tyr—Arg—Lys—Met—Arg—Leu—Arg—Tyr—Pro—Val—Cys—NH$_2$ (cyclic S—S) |

Compounds (I) can be prepared by a solid phase synthetic method using an automatic peptide synthesizer. A solid phase support to which a peptide prepared by the solid phase method has been coupled is treated with hydrogen fluoride or TFA, whereby the peptide is liberated from the solid support, and at the same time, the protective groups at amino acid side chains are removed. The amidation of C-terminal amino acids can be performed with p-Methyl-Benzhydrylamine(BHA)-Resin (Applied Biosystems, Inc., Foster City, Calif., USA; hereinafter referred to as "ABI") in the case where a peptide synthesizer available from ABI is uesd, and with Rink Amide-Resin or Rink Amide-MBHA (4-methylbenzhydrylamine)-Resin (available from Carbiochem-Novabiochem Japan) in the case where a peptide synthesizer available from Shimadzu is used. The modification (acylation) of N-terminal amino acids can be performed by removal of N-terminal amino acid protective groups, followed by condensation with a carboxylic acid component using a condensation agent such as PyBOP/HOBt/NMM in the same manner as in extension of peptide chains, or by condensation with an activated carboxylic acid such as an anhydride of a carboxylic acid and an acid chloride. The aforementioned reactions are conducted on a synthetic resin and the desired peptide derivative is obtained by cleaving it from the resin after the end of the reaction. The crude peptide product thus obtained is purified by high performance liquid chromatography (hereinafter referred to as "HPLC") using a reversed-phase column to yield a purified product.

Furthermore, cyclic peptides having an S—S bond can be obtained if linear peptides obtained in the above manner are air-oxidized in an aqueous solution of a weak base, or oxidized with an oxidizing agent such as potassium ferrocyanide or glutathione (oxidized form).

Compounds (I) provided by the present invention exhibit an excellent PLC-inhibiting activity, cell proliferation-inhibiting activity and antimicrobial activity.

The PLC-inhibiting activity, cell proliferation-inhibiting activity and antimicrobial activity of Compounds (I) are illustrated in the following Experimental Examples 1, 2 and 3, respectively.

EXPERIMENTAL EXAMPLE 1
PLC-INHIBITING ACTIVITY

A sample of PLC-$\gamma_1$ was prepared from bovine thymus according to the method described in Y. Homma et al., Biochem.J., 269, 13 (1990).

A solution having the composition shown in Table 2 was prepared on ice and the reaction was initiated by heating it to 37° C. After incubation for 10 minutes, 2 ml of a chloroform-methanol (2:1, V/V) mixed solution was added to stop the reaction. The produced inositol phosphate was extracted with 0.5 ml of 1N hydrochloric acid. The extract was separated into two liquid phases by centrifugation (2000×g, 3 minutes) and the amount of $^3$H in the supernatant (0.7 ml) was measured with a scintillation counter.

TABLE 2

| Solution | Volume ($\mu$l) |
|---|---|
| Sample (0.2 $\mu$g of Purified PI-PLC-$\gamma_1$ preparation) | 10 |
| Reaction solution | 30 |
| 1) 1M MES[a] NaOH buffer (pH 6.0) | 2.5 |
| 2) 1 mM CaCl$_2$ | 5 |
| 3) 20 mg/ml Bovine serum albumin | 2.5 |
| 4) Test peptide solution[b] | 20 |
| Substrate[c] | 10 |

[a] 2-(N-Morpholino)ethanesulfonic acid
[b] The test peptides and their concentrations in aqueous solution are shown in Table 3.
[c] Phosphatidylinositol 4,5-bisphosphoric acid (PIP$_2$) (500 $\mu$g), phosphatidylethanolamine (150 $\mu$g) and [$^3$H]PIP$_2$ (37 kBg) were mixed in a small amount of chloroform. After drying lipids under a nitrogen stream, 1 ml of 0.1M KCl was added and sonication was performed.

Percent inhibition (X) was calculated from the following equation.

$$X(\%)=(A-C)/(B-C)\times 100$$

where A is the obtained value of specific radioactivity, B is the value of specific radioactivity when the same amount of water was added instead of an aqueous solution of a test peptide, and C is the value of specific radioactivity when the same amount of water was added instead of a sample and an aqueous solution of a test peptide.

The thus determined percent inhibitions by the test peptides are shown in Table 3.

TABLE 3

| Compound | Concentration (μM) | Inhibition (%) |
|---|---|---|
| (I-2) | 240 | 65 |
| (I-4) | 220 | 56 |

EXPERIMENTAL EXAMPLE 2
CELL PROLIFERATION-INHIBITING ACTIVITY

The cell proliferation-inhibiting activity of the test peptides was determined using a cell proliferation-detecting kit available from Amersham in the following manner.

KMS-4 cells (M. Nanba et al., International Journal of Cancer, 32, 697 (1983)) were added to a DMEM medium containing a 10% fetal calf serum (available from Nissui Pharmaceutical) and the cell concentration was adjusted to $1-2 \times 10^4$ cells/ml. The resulting cell suspension (1 ml) was then placed in each well of a 24-well plate (available from Corning) and incubated in a $CO_2$ incubator (37° C., 5% $CO_2$) for 2 days. Subsequently, the medium was replaced with a fresh DMEM medium containing a 10% fetal calf serum, and a test peptide was added, followed by incubation for 17 hours. Then, the medium was replaced with a serum-free DMEM medium, and 0.5 ml of a solution prepared by diluting labeled 5-bromo-2'-deoxyuridine reagents (BrdU) and 5-fluoro-2'-deoxyuridine (FdU) (10:1) 1000 times with a serum-free DMEM was added to each well, followed by incubation for 2 hours. Then, the medium was removed and the cells were fixed with an acetic acid-ethanol solution. The fixed cells were stained according to the procedure for a cell proliferation-detecting kit available from Amersham and further stained with a 1% Giemsa solution (available from Merck). The number of cells which incorporated BrdU and the total number of cells were counted within one visual field (about 200 cells) under microscopic examination and the percentage (%) of the stained cell counts per visual field was calculated. The above procedure was repeated 10 more times and the mean value was taken to show the cell proliferation activity (%).

Cell proliferation-inhibiting activity was expressed by percent cell proliferation inhibition (X) which was calculated from the following equation.

$$X(\%) = (1 - B/A) \times 100$$

where A is the proliferation activity when no peptide was added, and B is the proliferation activity when a test peptide was added.

The thus determined percent cell proliferation inhibitions by the test peptides are shown in Table 4.

TABLE 4

| Compound | Concentration (μM) | Inhibition (%) |
|---|---|---|
| (I-2) | 5 | 59 |
| (I-4) | 6 | 61 |

EXPERIMENTAL EXAMPLE 3
ANTIMICROBIAL ACTIVITY

Antimicrobial activity was determined by an agar dilution method using a medium consisting of Bacto-tryptone (available from Difco) (3 g/l), meat extract (1 g/l), glucose (1 g/l) and agar (16 g/l) (pH 7.0).

When *Proteus vulgaris* ATCC6897 was used as a test bacterium, the minimum inhibitory concentrations (MIC) of Compounds (I-3) and (I-4) were each 166 μg/ml.

BEST MODE FOR CARRYING OUT THE INVENTION

The physicochemical properties shown in the following examples were measured with the apparatus listed below.

Mass spectrometric analysis: Nihon Denshi JMS-HXL110A

Amino acid analysis: Waters pico tag

The following Examples 1–4 will illustrate peptide synthesis using the peptide synthesizer PSSM8 available from Shimadzu with reagents and solvents available from Shimadzu according to a synthesis program developed by Shimadzu. Amino acid condensation reactions were conducted by the Fmoc method (Peptide Synthesis—Its Fundamentals and Experiments, Nobuo Izumiya, et al., (Maruzen)) under standard conditions.

Protected amino acids and reagents available from Kokusan Kagaku, Peptide Institute, Carbiochem-Novabiochem Japan were used as required.

EXAMPLE 1
Synthesis of Compound (I-1: SEQ ID NO:1)

A support resin (60 mg) combined with 4-(2,4-dimethoxyphenyl-Fmoc-aminomethyl)-phenoxy group was placed in a reactor in an automatic peptide synthesizer, treated and washed according to the synthesis program developed by Shimadzu in the following manner:

(1) Washing with DMF (3 min)

(2) Treating with a DMF solution containing 30% piperidine (4 min×2)

(3) Washing with DMF (1 min×5)

(4) Adding Fmoc-Cys(Trt)-OH (300 μmol), PyBOP (300 μmol), HOBT (300 μmol), and NMM (450 μmol) to the support resin treated in steps (1) to (3), and stirring the mixture for 30 minutes.

(5) Washing with DMF (1 min×5)

Thus, Fmoc-Cys(Trt) was coupled to the support.

Subsequently, washing and deprotection steps (1)–(3) were performed and a condensation reaction was then conducted using Fmoc-Val-OH in step (4), followed by washing step (5) to couple Fmoc-Val-Cys(Trt) to the support resin. Steps (1)–(5) were sequentially repeated using 300 μmol of Fmoc-Pro-OH, Fmoc-Tyr(t-Bu)-OH, Fmoc-Arg(Pmc)-OH, Fmoc-Leu-OH, Fmoc-Arg(Pmc)-OH, Fmoc-Met-OH, Fmoc-Lys(t-Boc)-OH, Fmoc-Arg(Pmc)-OH, Fmoc-Tyr(t-Bu)-OH, Fmoc-Leu-OH, and Fmoc-Cys(Trt)-OH in step (4) to give a protected peptide coupled to the support resin.

The obtained support resin was then washed thoroughly with methanol and butylether and dried for 2 hours under reduced pressure. One milliliter of 10% TFA/methylene chloride was charged into the reactor containing the dried support resin, followed by stirring. A solution was collected by dropping under gravity from the bottom of the reactor. The above procedure was repeated twice except that 1 ml of 20% TFA/methylene chloride was added. Removal of the solvent from the collected solutions with an evaporator gave a peptide cleaved from the resin. Furthermore, the peptide was deprotected by adding 1 ml of a mixed solution consisting of 82.5% TFA, 5% $H_2O$, 5% thioanisole, 2.5% ethanedithiol, 3% ethylmethylsulfide, and 2% thiophenol and leaving the mixture to stand for 8 hours at room temperature. About 2 ml of ether was added to the resulting solution to precipitate a crude peptide. The collected crude peptide (52.6 mg) was purified by HPLC using a reversed-phase column (NUCLEOSIL 5C18, 20×250 mm). A fraction containing the desired compound was obtained by elution with a linear concentration gradient of acetonitrile in water containing 0.1% TFA and detection at a wavelength of 220 nm. The fraction was lyophilized to yield Compound (I-1) (16.5 mg).

Mass spectrometric analysis: M+H=1699

Amino acid analysis: Arg 3.1 (3), Pro 1.0 (1), Tyr 2.0 (2), Val 0.9 (1), Met 1.0 (1), Leu 2.0 (2), Lys 1.1 (1), Cys 1.8 (2)

EXAMPLE 2
Synthesis of Compound (I-2: SEQ ID NO:2)

Compound (I-1) (15.6 mg) was dissolved in 15.6 ml of water. To the resulting solution were added 1.56 ml of 200 mM phosphate buffer (pH 7.0) and 0.32 ml of 10 mM glutathione (oxidized form) and cyclization reaction was conducted at 4° C. for 19 hours. The cyclized product was purified by HPLC to yield Compound (I-2) (3.6 mg).

Mass spectrometric analysis: M+H=1697

Amino acid analysis: Arg 3.1 (3), Pro 1.0 (1), Tyr 2.0 (2), Val 0.9 (1), Met 1.0 (1), Leu 2.0 (2), Lys 1.1 (1), Cys 1.8 (2)

EXAMPLE 3
Synthesis of Compound (I-3: SEQ ID NO:3)

Condensation reaction was performed as in Example 1 using 60 mg of the support resin and the following N-protected amino acids: Fmoc-Cys(Trt)-OH, Fmoc-Val-OH, Fmoc-Pro-OH, Fmoc-Tyr(t-Bu)-OH, Fmoc-Arg (Pmc)-OH, Fmoc-Leu-OH, Fmoc-Arg(Pmc)-OH, Fmoc-Met-OH, Fmoc-Lys(t-Boc)-OH, Fmoc-Arg(Pmc)-OH, Fmoc-Tyr(t-Bu)-OH, Fmoc-Leu-OH, and Fmoc-Cys(Trt)-OH and n-caprylic acid. As in Example 1, a peptide was cleaved from the resin and deprotected to yield a crude product (62.4 mg). A portion (25.4 mg) of the crude product was purified by HPLC to yield Compound (I-3) (21.5 mg).

Mass spectrometric analysis: M+H=1825

Amino acid analysis: Arg 3.0 (3), Pro 1.0 (1), Tyr 2.0 (2), Val 0.9 (1), Met 1.0 (1), Leu 2.0 (2), Lys 1.0 (1), Cys 2.0 (2).

EXAMPLE 4
Synthesis of Compound (I-4: SEQ ID NO:4)

Compound (I-3) (9.0 mg) was dissolved in 9 ml of water. To the resulting solution were added 1 ml of 200 mM phosphate buffer (pH 7.0), 0.4 ml of 10 mM glutathione (oxidized form) and 18 ml of 9M urea and cyclization reaction was conducted at 4° C. for 45 hours. The cyclized product was purified by HPLC to yield Compound (I-4) (4.1 mg).

Mass spectrometric analysis: M+H=1823

Amino acid analysis: Arg 3.0 (3), Pro 1.0 (1), Tyr 2.0 (2), Val 0.9 (1), Met 1.0 (1), Lys 1.0 (1), Cys 2.0 (2)

INDUSTRIAL APPLICABILITY

According to the present invention, peptides having the phospholipase C-inhibiting activity can be provided.

---

We claim:

1. A phospholipase C-inhibiting peptide which is represented by formula (I):

$$\text{W}-\text{Cys}-\text{X}-\text{Tyr}-\text{Arg}-\text{Lys}-\text{Met}-\text{Arg}-\text{Leu}-\text{Arg}-\text{Tyr}-$$
$$\qquad\quad |\\ \qquad\quad \text{J}^1$$

-continued

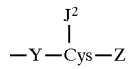

wherein $J^1$ and $J^2$ are each hydrogen or combined together to form a single bond; W is hydrogen, an alkanoyl having from 1 to 20 carbon atoms, an aroyl or coumaryl; X is a single bond, -Leu- or -Ser-Leu-Val-Glu-Leu-Val-Ser-Tyr-Tyr-Glu-Lys-His-Ala-Leu- wherein at least one of the N-terminal 14 amino acid residues may be deleted; Y is a single bond or -Pro-Val-; and Z is hydroxy or amino, with the proviso that when $J^1$ and $J^2$ are each hydrogen W is an alkanoyl having from 1 to 20 carbon atoms, an aroyl or coumaryl.

2. The peptide of claim 1, wherein X is -Leu- and Y is -Pro-Val-.

3. The peptide of claim 2, wherein Z is amino.

4. The peptide of claim (1), (2) or (3), wherein said peptide is selected from the group consisting of peptides having amino acid sequences shown by SEQ. ID Nos. 2 (compound I-2), 3 (compound I-3) and 4 (compound I-4).

5. The peptide according to claim 1 wherein the alkanoyl is selected from the group consisting of formyl, acetyl, propionyl, butyryl, isobutyryl, valeryl, isovaleryl, pivaloyl, caprylyl, lauroyl, myristoyl, palmitoyl, and stearoyl.

6. The peptide according to claim 1 wherein the alkanoyl is substituted with an alicyclic alkyl having 3 to 8 carbon atoms.

7. The peptide according to claim 6 wherein the alicyclic alkyl is selected from the group consisting of cyclopropyl, cyclobutyl, cyclopentyl and cyclohexyl.

8. The peptide according to claim 1 wherein the aroyl is selected from the group consisting of benzoyl and naphthoyl.

9. The peptide according to claim 1 wherein the aroyl is substituted with 1 to 3 hydroxy groups.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 13
        ( B ) TYPE: AMINO ACID
        ( D ) TOPOLOGY: LINEAR ( i i ) MOLECULE TYPE: PEPTIDE ( i x ) FEATURE:
        ( A ) NAME/KEY: MODIFIED-SITE
        ( B ) LOCATION: 13
        ( C ) IDENTIFICATION METHOD: EXPERIMENT
        ( D ) OTHER INFORMATION: XAA AT LOCATION 13
            IS L- CYSTEINAMIDE ( x i ) SEQUENCE DESCRIPTION:SEQ ID NO:1:

Cys Leu Tyr Arg Lys Met Arg Leu Arg Tyr Pro Val Xaa
1               5                             10

( 2 ) INFORMATION FOR SEQ ID NO:2:

( i ) SEQUENCE CHARACTERISTICS:
        ( A ) LENGTH: 13
        ( B ) TYPE: AMINO ACID
        ( D ) TOPOLOGY: LINEAR ( i i ) MOLECULE TYPE: PEPTIDE ( i x ) FEATURE:
        ( A ) NAME/KEY: DISULFIDE-BONDS
        ( B ) LOCATION: 1..13

(C) IDENTIFICATION METHOD: EXPERIMENT
(D) OTHER INFORMATION: XAA AT LOCATION 13
     IS L- CYSTEINAMIDE (xi) SEQUENCE DESCRIPTION:SEQ ID NO:2:

Cys Leu Tyr Arg Lys Met Arg Leu Arg Tyr Pro Val Xaa
1               5                       10

(2) INFORMATION FOR SEQ ID NO:3:

(i) SEQUENCE CHARACTERISTICS:
    (A) LENGTH: 13
    (B) TYPE: AMINO ACID
    (D) TOPOLOGY: LINEAR (ii) MOLECULE TYPE: PEPTIDE (ix) FEATURE:
    (A) NAME/KEY: MODIFIED-SITE
    (B) LOCATION: 1
    (C) IDENTIFICATION METHOD: EXPERIMENT
    (D) OTHER INFORMATION: XAA AT LOCATION 1 IS
         N-(N- CAPRYLOYL) - L-CYSTEINE (ix) FEATURE:
    (A) NAME/KEY: MODIFIED-SITE
    (B) LOCATION: 13
    (C) IDENTIFICATION METHOD: EXPERIMENT
    (D) OTHER INFORMATION: XAA AT LOCATION 13
         IS L- CYSTEINAMIDE (xi) SEQUENCE DESCRIPTION:SEQ ID NO:3:

Xaa Leu Tyr Arg Lys Met Arg Leu Arg Tyr Pro Val Xaa
1               5                       10

(2) INFORMATION FOR SEQ ID NO:4:

(i) SEQUENCE CHARACTERISTICS:
    (A) LENGTH: 13
    (B) TYPE: AMINO ACID
    (D) TOPOLOGY: LINEAR (ii) MOLECULE TYPE: Peptide (ix) FEATURE:
    (A) NAME/KEY: DISULFIDE-BONDS
    (B) LOCATION: 1..13
    (C) IDENTIFICATION METHOD: EXPERIMENT (ix) FEATURE:
    (A) NAME/KEY: MODIFIED-SITE
    (B) LOCATION: 1
    (C) IDENTIFICATION METHOD: EXPERIMENT
    (D) OTHER INFORMATION: XAA AT LOCATION 1
         IS N -(N- CAPRYLOYL)-L-CYSTEINE (ix) FEATURE:
    (A) NAME/KEY: MODIFIED-SITE
    (B) LOCATION: 13
    (C) IDENTIFICATION METHOD: EXPERIMENT
    (D) OTHER INFORMATION: XAA AT LOCATION 13
         IS L- CYSTEINAMIDE (xi) SEQUENCE DESCRIPTION:SEQ ID NO:4:

Xaa Leu Tyr Arg Lys Met Arg Leu Arg Tyr Pro Val Xaa
1               5                       10